United States Patent
Kaiser

(10) Patent No.: US 8,423,141 B2
(45) Date of Patent: Apr. 16, 2013

(54) PRE-EXCITATION STIMULUS TIMING BASED ON MECHANICAL EVENT

(75) Inventor: Daniel R. Kaiser, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 983 days.

(21) Appl. No.: 12/363,147

(22) Filed: Jan. 30, 2009

(65) Prior Publication Data

US 2010/0198294 A1   Aug. 5, 2010

(51) Int. Cl.
*A61N 1/365*   (2006.01)

(52) U.S. Cl.
USPC .............................................. 607/17; 607/18

(58) Field of Classification Search ................ 607/1–37; 600/483
See application file for complete search history.

(56) References Cited

U.S. PATENT DOCUMENTS

| | | | |
|---|---|---|---|
| 5,507,782 A | 4/1996 | Kieval et al. | |
| 5,626,620 A | 5/1997 | Kieval et al. | |
| 5,626,623 A | 5/1997 | Kieval et al. | |
| 5,700,283 A | 12/1997 | Salo | |
| 5,716,383 A | 2/1998 | Kieval et al. | |
| 5,749,906 A | 5/1998 | Kieval et al. | |
| 6,507,756 B1 | 1/2003 | Heynen et al. | |
| 6,829,505 B2 | 12/2004 | Kramer et al. | |
| 6,915,160 B2 | 7/2005 | Auricchio et al. | |
| 6,965,797 B2 | 11/2005 | Pastore et al. | |
| 6,973,349 B2 | 12/2005 | Salo | |
| 7,010,347 B2 | 3/2006 | Schecter | |
| 7,041,061 B2 | 5/2006 | Kramer et al. | |
| 7,065,405 B2 | 6/2006 | Pastore et al. | |
| 7,079,896 B1 | 7/2006 | Park et al. | |
| 7,103,410 B2 | 9/2006 | Kramer et al. | |
| 7,110,817 B2 | 9/2006 | Yu et al. | |
| 7,158,824 B2 | 1/2007 | Girouard et al. | |
| 7,158,830 B2 | 1/2007 | Yu et al. | |
| 7,181,284 B2 | 2/2007 | Burnes et al. | |
| 7,260,431 B2 | 8/2007 | Libbus et al. | |
| 7,346,394 B2 | 3/2008 | Liu et al. | |
| 7,366,567 B2 | 4/2008 | Zhu et al. | |
| 7,389,141 B2 | 6/2008 | Hall et al. | |
| 7,392,084 B2 | 6/2008 | KenKnight et al. | |
| 7,450,988 B2 | 11/2008 | Ross et al. | |
| 2004/0019365 A1 | 1/2004 | Ding et al. | |
| 2005/0065568 A1* | 3/2005 | Liu et al. ......................... | 607/17 |
| 2005/0288720 A1 | 12/2005 | Ross et al. | |

(Continued)

OTHER PUBLICATIONS

P0032230.01 (PCT/US2010/022190) PCT Notification of Transmittal of the International Search Report and the Written Opinion of the International Searching Authority, Jun. 2010.

*Primary Examiner* — George Evansko
*Assistant Examiner* — Lindsey G Hankins
(74) *Attorney, Agent, or Firm* — Reed A. Duthler; Stephen W. Bauer

(57) ABSTRACT

Techniques for determining when to deliver a pre-excitation signal to damaged cardiac tissue, e.g., infarct tissue, of a ventricle during cardiac pacing are described. A medical device detects an intrinsic or paced atrial depolarization, and then detects a subsequent mechanical event, e.g., contraction, in a ventricle. As examples, the mechanical event may be detected by measuring ventricular movement, or changes in intracardiac or systemic blood pressure. The medical device determines an interval between the atrial depolarization and the ventricular mechanical event, which may be referred to as an $A\text{-}V_m$ interval. By subtracting a pre-excitation interval (PEI) from the $A\text{-}V_m$, the medical device determines an A-V interval between an atrial depolarization and delivery of the pre-excitation signal.

16 Claims, 9 Drawing Sheets

U.S. PATENT DOCUMENTS

| | | |
|---|---|---|
| 2006/0217773 A1* | 9/2006 | Zhu et al. .................. 607/9 |
| 2006/0276847 A1* | 12/2006 | Yu et al. .................. 607/9 |
| 2006/0287683 A1 | 12/2006 | Pastore et al. |
| 2007/0055317 A1 | 3/2007 | Stahmann et al. |
| 2007/0078507 A1 | 4/2007 | Zacouto |
| 2007/0191891 A1 | 8/2007 | Burnes et al. |
| 2007/0191892 A1 | 8/2007 | Mullen et al. |
| 2008/0004669 A1 | 1/2008 | Sathaye et al. |
| 2008/0082135 A1 | 4/2008 | Arcot-Krishnamurthy et al. |
| 2008/0114407 A1 | 5/2008 | Pastore et al. |
| 2008/0234772 A1 | 9/2008 | Shuros et al. |
| 2008/0234774 A1 | 9/2008 | Baynham et al. |
| 2008/0234776 A1 | 9/2008 | KenKnight et al. |
| 2008/0269823 A1 | 10/2008 | Burnes et al. |

* cited by examiner

PRE-EXCITATION STIMULUS TIMING BASED ON MECHANICAL EVENT

TECHNICAL FIELD

The disclosure relates to implantable medical devices, and, more particularly, to the timing of therapeutic cardiac pacing signals.

BACKGROUND

Due to a variety of medical conditions, intrinsic cardiac depolarization may diminish in its ability to cause a coordinated mechanical contraction of the heart sufficient to provide adequate blood flow from the heart. These medical conditions may include dysfunctions of the sinus node, atrioventricular node, or the electrical conduction pathways in the heart, e.g., the Bundle of His and Purkinje fibers. When cardiac output is limited due to such a dysfunction, a patient may turn to medical intervention to alleviate the problem and restore normal cardiac function.

Commonly, such dysfunctions may be treated with an artificial pacemaker that regulates the function of the heart. An artificial pacemaker is a medical device that generates and delivers electrical impulses to the patient's heart to regulate the contraction of cardiac muscle. The electrical impulses are generally delivered to one or more locations within the heart to effectively depolarize the cardiac muscle. In this manner, the pacemaker manages the timing of atrial and ventricular contraction to adequately pump blood throughout the systemic and pulmonary vasculature.

In some patients, one or more areas of the cardiac muscle have been damaged due to ischemia caused by coronary artery disease that prevented adequate blood flow to the cardiac tissue. Such damaged areas are referred to as myocardial infarctions. Infarct tissue does not contract when stimulated in the same manner as healthy cardiac muscle does. Instead, the infarct tissue expands and thins while the rest of the heart is thickening during each cardiac cycle. Non-uniform contraction of cardiac muscle can lead to infarct expansion and overall remodeling of the heart. Remodeling of the heart can lead to cardiac muscle dysfunction, cardiac conduction dysfunction, decreased cardiac output and, eventually, heart failure.

SUMMARY

In general, this disclosure is directed to techniques for determining when to deliver a pre-excitation stimulus to infarct tissue within a ventricle of a heart. A pre-excitation stimulus delivered to, or very near, the infarct tissue activates the slower reacting infarct tissue before the remaining healthy myocardium contracts. In this manner, the pre-excitation stimulus reduces stress at the infarct site, thereby inhibiting long term expansion of the damage and remodeling of the heart.

To determine the appropriate time to deliver the pre-excitation stimulus, a medical device detects an intrinsic or paced atrial depolarization, and then detects a subsequent mechanical event, e.g., onset of contraction, in a ventricle. As examples, the mechanical event may be detected by measuring ventricular movement, or changes in intra-cardiac or systemic blood pressure. The medical device determines an interval between the atrial depolarization and the ventricular mechanical event, which may be referred to as an A-$V_m$ interval.

By subtracting a pre-excitation interval (PEI) from the A-$V_m$, the medical device determines an A-V interval between an atrial depolarization and delivery of the pre-excitation stimulus. The medical device delivers, or controls delivery of, a pre-excitation stimulus to the infarct tissue according to this A-V interval. If necessary, the PEI may be adjusted to appropriately pre-excite the damaged tissue relative to the healthy tissue in the heart.

In one example, the disclosure provides a method comprising detecting a mechanical ventricular event during a cardiac cycle of a heart, determining a timing of the detected mechanical ventricular during the cardiac cycle, determining a time for delivery of a pre-excitation stimulus to infarct tissue in a ventricle of the heart during a subsequent cardiac cycle based on the detected mechanical ventricular event, and delivering the pre-excitation stimulus to the infarct tissue at the determined time during the subsequent cardiac cycle.

In another example, the disclosure provides a system comprising a medical device configured to deliver a pre-excitation stimulus to infarct tissue in a ventricle of a heart of a patient, a sensor configured to generate a signal that varies as a function of mechanical ventricular activity and a processor configured to detect a mechanical ventricular event during a cardiac cycle of the heart based on the sensor signal, determine a timing of the detected mechanical ventricular during the cardiac cycle, determine a time for delivery of the pre-excitation stimulus during a subsequent cardiac cycle based on the detected mechanical ventricular event, and control the medical device to deliver the pre-excitation stimulus to the infarct tissue at the determined time during the subsequent cardiac cycle.

In another example, the disclosure provides a system comprising means for detecting a mechanical ventricular event during a cardiac cycle of a heart, means for determining a timing of the detected mechanical ventricular during the cardiac cycle, means for determining a time for delivery of a pre-excitation stimulus to infarct tissue in a ventricle of the heart during a subsequent cardiac cycle based on the detected mechanical ventricular event, and means for delivering the pre-excitation stimulus to the infarct tissue at the determined time during the subsequent cardiac cycle.

DETAILED DESCRIPTION

A medical device, such as an implantable pacemaker, cardioverter, defibrillator, pacemaker-cardioverter-defibrillator, or another implantable medical device (IMD), detects a mechanical event, e.g., onset of contraction, of the ventricles. The medical device determines an A-V interval for delivery of pre-excitation stimuli to infarct tissue in the ventricles based on the mechanical event detection. The mechanical event may be any mechanical event associated with ventricular movement that produces blood flow out of the ventricles. Example techniques for detecting the mechanical event include measuring systemic blood pressure, measuring intra-ventricular pressure, sensing motion of a lead attached to the heart, or sensing ventricle wall motion. These methods of detecting the mechanical event may be performed by sensors attached to cardiac leads or otherwise electrically or wirelessly coupled to the medical device.

Figure 1:
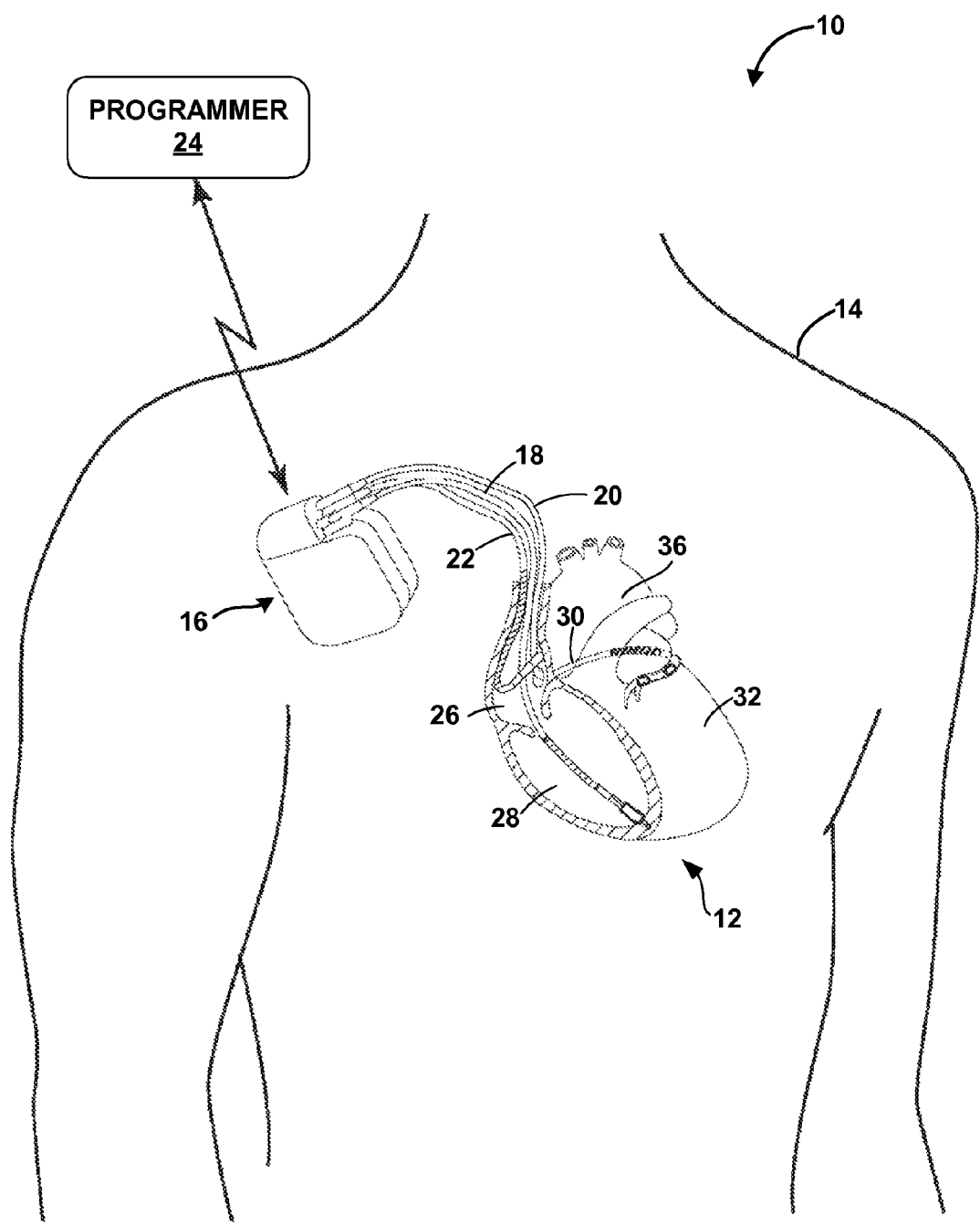
FIG. 1 is a conceptual drawing illustrating an example system that includes an implantable medical device (IMD) coupled to implantable medical leads.

FIG. 1 is a conceptual drawing illustrating an example system 10 that includes an implantable medical device (IMD) 16 coupled to implantable medical leads 18, 20, and 22. System 10 includes IMD 16, which is coupled to leads 18, 20, and 22, and programmer 24. IMD 16 may be, for example, an implantable pacemaker, cardioverter, and/or defibrillator that delivers therapeutic electrical signals to heart 12 via electrodes coupled to one or more of leads 18, 20, and 22.

Leads 18, 20, 22 extend into the heart 12 of patient 16. IMD 16 senses electrical signals attendant to the depolarization and repolarization of heart 12 via electrodes (not shown in FIG. 1) coupled to at least one of the leads 18, 20 and 22. IMD also delivers electrical stimulation to heart 12 via selected combinations of the electrodes coupled to leads 18, 20 and 22.

As described herein, the electrical stimulation includes pre-excitation stimuli to pre-excite infarct tissue relative to the contraction of other healthy tissue in the heart. The electrical stimulation may also include cardiac pacing, cardioversion and/or defibrillation signals. The configurations of electrodes used by IMD 16 for sensing and stimulation may be unipolar or bipolar.

In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 additionally or alternatively includes one or more leads or lead segments (not shown in FIG. 1) that deploy one or more electrodes within the left atrium, vena cava, or another vein. In some examples, system 10 additionally or alternatively includes temporary or permanent epicardial or subcutaneous leads, instead of or in addition to leads 18, 20 and 22. Electrodes carried by such leads may be used for one or more of cardiac sensing, cardiac pacing, cardioversion/defibrillation, or delivery of pre-excitation stimuli according to the techniques described herein with respect to leads 18, 20 and 22.

Programmer 24 is configured to wirelessly communicate with IMD 16. IMD 16 and programmer 24 may wirelessly communicate using any techniques known in the art. Examples of communication techniques may include, for example, low frequency or radiofrequency (RF) telemetry, but other techniques are also contemplated. In some examples, programmer 24 includes a programming head that includes an antenna and may be placed proximate to the patient's body near the IMD 16 implant site to facilitate communication between IMD 16 and programmer 24.

In some examples, programmer 24 may be a handheld computing device, computer workstation, or networked computing device. Programmer 24 includes a user interface that presents information to and receives input from a user. A user, such as a physician, technician, surgeon, electrophysiologist, or other clinician, interacts with programmer 24 to communicate with IMD 16.

For example, the user may interact with programmer 24 to retrieve physiological or diagnostic information from IMD 16. A user may also interact with programmer 24 to program IMD 16, e.g., select values for operational parameters of the IMD. For example, a user may interact with programmer 24 to review diagnostic information and evaluate the efficacy of pre-excitation stimulation delivered by IMD 16, as well as to program or control various aspects of the pre-excitation stimulation.

Figure 2:
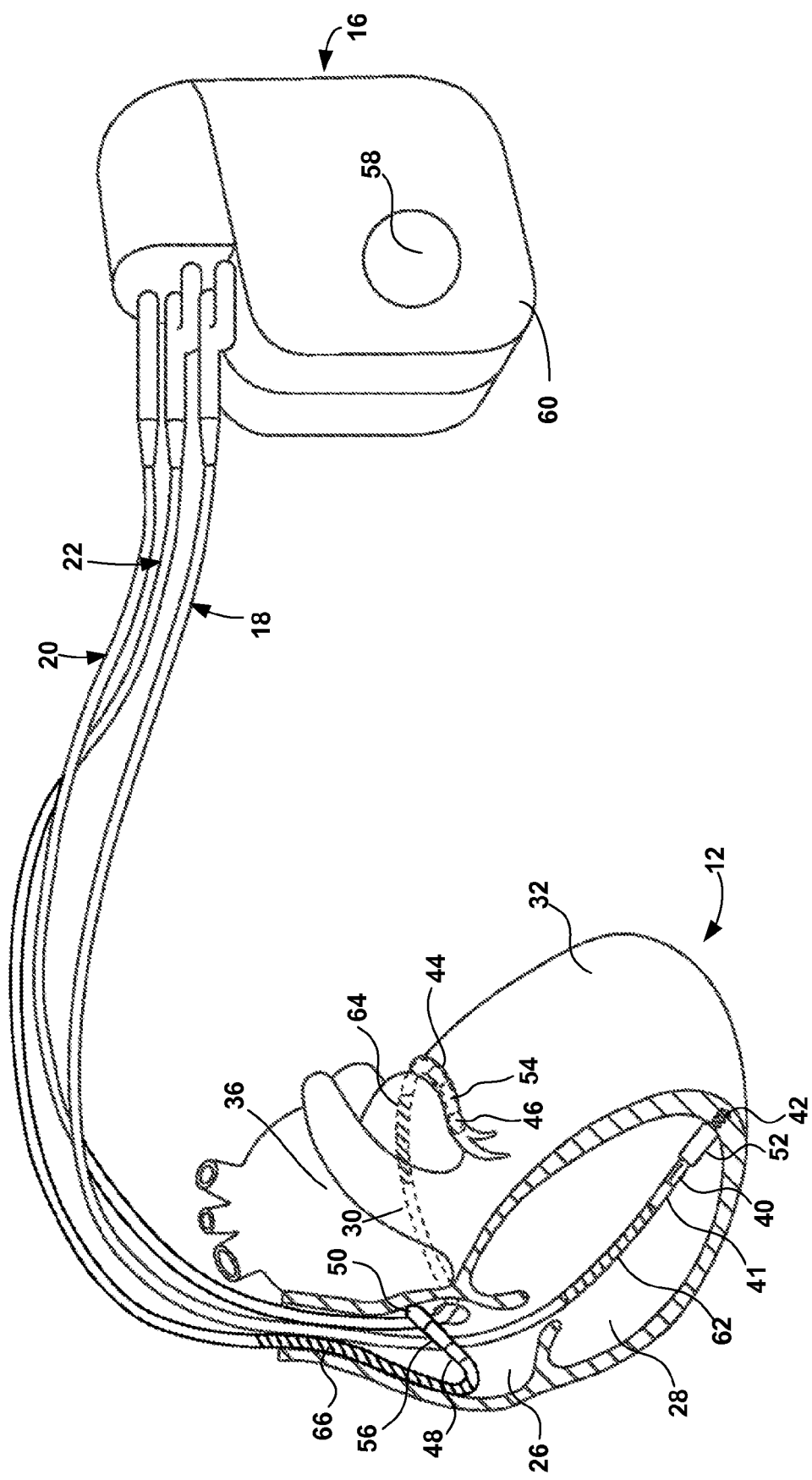
FIG. 2 is a conceptual drawing illustrating the example IMD and leads of FIG. 1 in conjunction with a heart.

FIG. 2 is a conceptual drawing illustrating IMD 16 and leads 18, 20 and 22 of system 10 in greater detail. Leads 18, 20, 22 are electrically coupled to a signal generator, e.g., stimulation generator, and a sensing module of IMD 16. Each of the leads 18, 20, 22 includes one or more elongated conductors that couple one or more electrodes to the signal generator and sensing module.

Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the conductors within the lead body of its associated lead 18, 20, 22, and thereby coupled to the signal generator and sensing module of IMD 16.

In some examples, IMD 16 includes one or more housing electrodes, such as housing electrode 58 illustrated in FIG. 2, formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44, 46, 48, 50, 62, 64 and 66. These electrical signals may be indicative of intrinsic atrial signals and/or ventricular signals. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58.

A system may include any suitable number of leads coupled to IMD 16, and each of the leads may extend to any location within or proximate to heart 12. For example, other examples of system 10 may include three transvenous leads located as illustrated in FIGS. 1 and 2, and an additional lead located within or proximate to left atrium 36. As another example, other examples of pacing systems may include a single lead that extends from IMD 16 into right atrium 26 or right ventricle 28, or two leads that extend into a respective one of the right ventricle 26 and right atrium 26.

Figure 3:
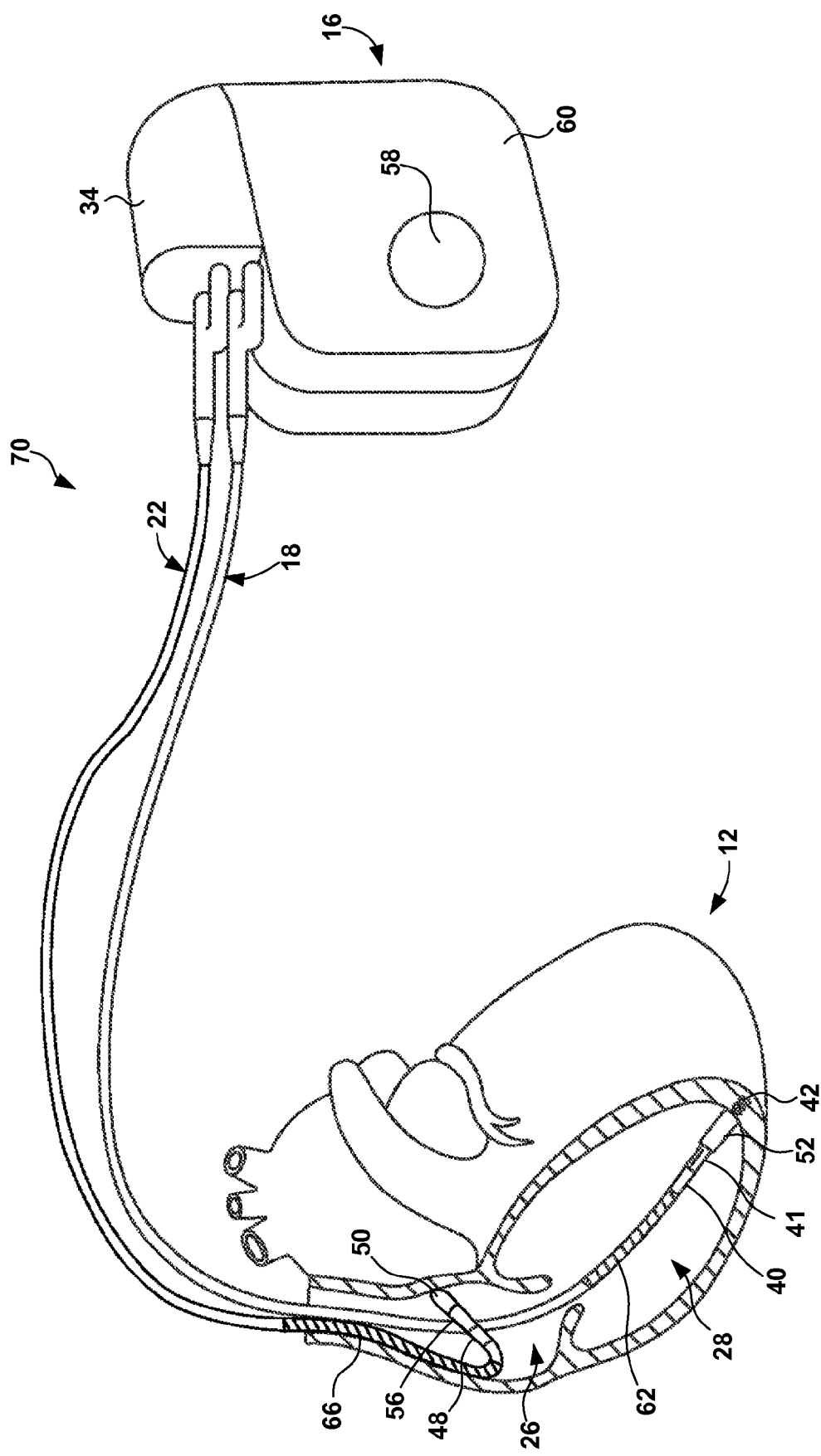
FIG. 3 is a conceptual drawing illustrating the example IMD of FIG. 1 coupled to a different example configuration of implantable medical leads in conjunction with a heart.

An example of an alternate system is shown in FIG. 3. FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively.

Whether the leads are configured as illustrated in FIGS. 2 and 3, or are otherwise configured, IMD 16 delivers pre-excitation stimulus to infarct tissue within the ventricles of heart 12, i.e., one of the RV or LV. One or more electrodes, such as one or more of electrodes 40, 42, 44, 46, or 64, are positioned proximate to the infarct tissue to deliver the stimulation to the infarct tissue, e.g., to tissue in the borderzone of ischemic myocardium. The positions of ventricular leads 18 and 20 within heart 12 are for purposes of illustration only, and either lead may be positioned as necessary in order to position an electrode proximate to the infarct tissue for delivery of pre-excitation stimuli. In examples ventricular pacing of healthy myocardium is also desired, an additional lead may be used to position an electrode proximate to the ischemic tissue. For example, lead 18 may be positioned as illustrated in FIGS. 2 and 3 to deliver RV pacing at the apex of heart 12, while another lead positions an electrode proximate to infarct tissue that is not near the apex for delivery of pre-excitation stimuli to the infarct tissue.

In the examples illustrated by FIGS. 2 and 3, lead 18 also includes a sensor 41. As will be described in greater detail below, IMD 16 detects a mechanical ventricular event, e.g., contraction, based on a signal generated by sensor 41. Although illustrated in FIGS. 2 and 3 as being located on lead 18, other example systems may include one or more sensors for detecting mechanical ventricular events, which may be located on any of leads 18, 20 and 22, or another lead. In some examples, a sensor for detecting mechanical ventricular events is wirelessly coupled to IMD 16.

Figure 4:
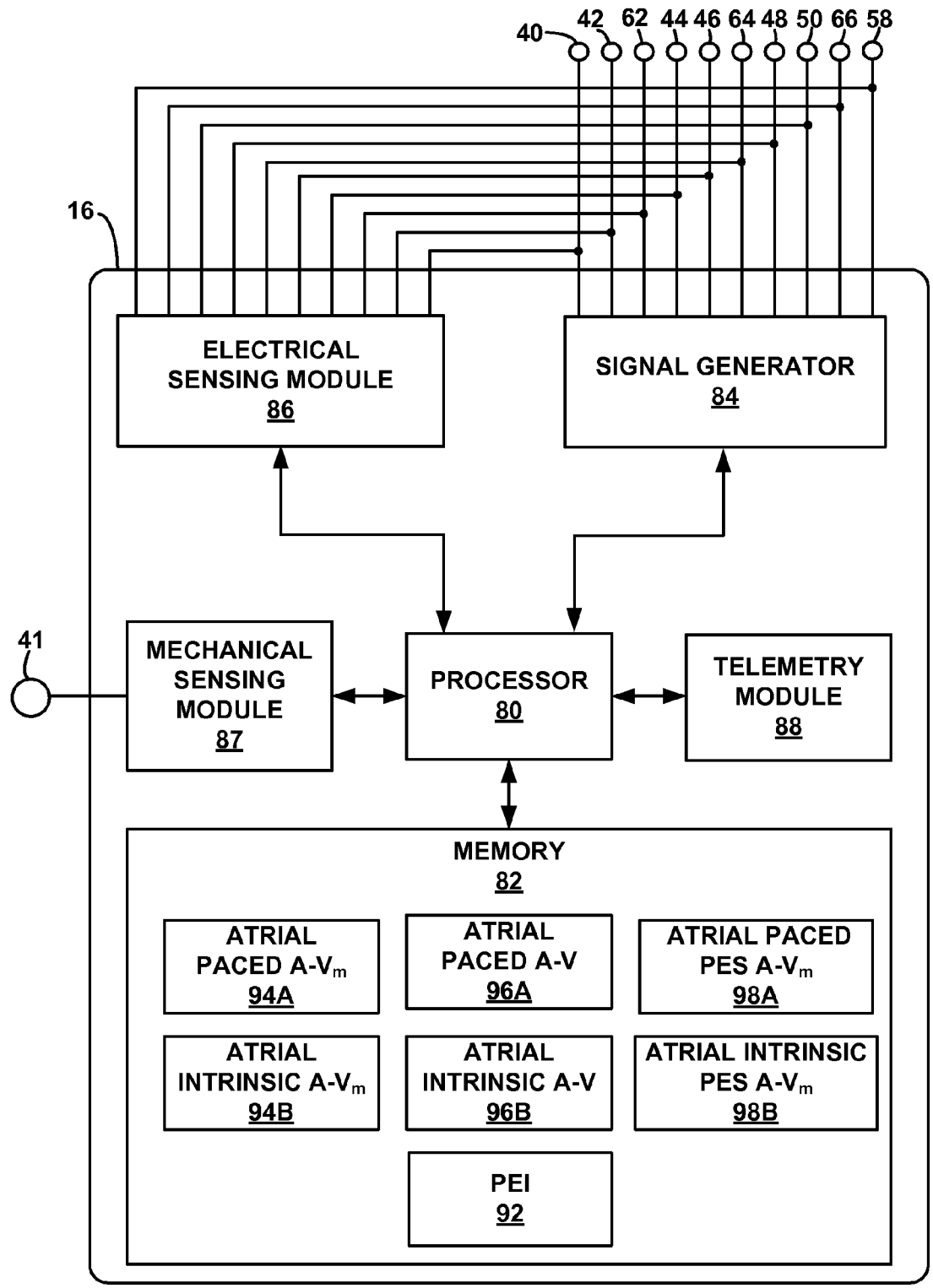
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, electrical sensing module 86, and telemetry module 88. IMD 16 also includes a mechanical sensing module 87 coupled to sensor 41.

Memory 82 includes computer-readable instructions that, when executed by processor 80, cause IMD 16, processor 80, and any other components of IMD 16 to perform various functions attributed to them herein. Memory 82 comprises any volatile, non-volatile, magnetic, optical, or electrical media, such as a random access memory (RAM), read-only memory (ROM), non-volatile RAM (NVRAM), electrically-erasable programmable ROM (EEPROM), or flash memory. Processor 80 comprises any one or more of a microprocessor, a controller, a digital signal processor (DSP), an application specific integrated circuit (ASIC), a field-programmable gate array (FPGA), or equivalent discrete or analog logic circuitry. In some examples, processor 80 includes multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware, or any combination thereof.

Processor 80 controls signal generator 84 to deliver electrical stimulation therapy to heart 12 according to a selected one or more of therapy programs, which may be stored in memory 82. Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Electrical stimulation therapy delivered by signal generator 84 includes pre-excitation stimulation and cardiac pacing, and may also include cardioversion and/or defibrillation. In some examples, signal generator 84 delivers pacing, cardioversion, defibrillation, or pre-excitation stimulation in the form of electrical pulses. In other examples, signal generator may deliver one or more of these types of stimulation in the form of other signals, such as sine waves, square waves, or other substantially continuous time signals.

In some examples, pre-excitation stimuli are substantially similar to pacing pulses. In some examples, a single pre-excitation stimulus is delivered to an infarct tissue region each cardiac cycle. Delivery of the pre-excitation stimuli may be suspended for monitoring as described below.

Signal generator 84 may include a switch module, and processor 80 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes.

Electrical sensing module 86 monitors signals from selected combinations of electrodes 40, 42, 44, 46, 48, 50, 58, 62, 64 or 66 in order to monitor electrical activity of heart 12. Sensing module 86 may also include a switch module, which processor 80 may use to select which of the available electrodes are used to sense the electrical cardiac activity. In one example, electrical sensing module 86 detects intrinsic atrial signals, e.g., P-waves, and processor 80 determines the timing of pre-excitation stimuli based on the intrinsic atrial signals.

Sensing module 86 includes one or more detection channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Different channels of sensing module 86 are used to sense either atrial or ventricular events, typically from a respective chamber of heart 12.

In one example, at least one channel includes an R-wave amplifier that receives signals from the sensing configuration of electrodes 40 and 42, which are used for sensing and/or pacing in right ventricle 28 of heart 12. Another channel may include another R-wave amplifier that receives signals from the sensing configuration of electrodes 44 and 46, which are used for sensing and/or pacing proximate to left ventricle 32 of heart 12. Another channel may include a P-wave amplifier that receives signals from electrodes 48 and 50, which are used for pacing and sensing in right atrium 26 of heart 12. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Mechanical sensing module 87 is coupled to sensor 41. Sensor 41 generates a signal that varies as a function of movement of the right and/or left ventricle of heart 12. Mechanical sensing module 87 conditions the signal for receipt by processor 80, and may include amplifiers, filters, an analog-to-digital converter, or the like. Processor 80 detects a mechanical event associated with movement of the right and/or left ventricle of heart 12, e.g., onset of ventricular contraction, based on the conditioned signal from sensor 41. The signal from sensor 41 is received by mechanical sensing module 87 and processed into a data signal usable by processor 80.

Although mechanical sensing module 87 may generally deliver continuous data to processor 80 for further processing, mechanical sensing module 87 may only deliver certain data to processor 80. For example, mechanical sensing module 87 may be configured to only send data from sensor 41 when the data is greater than a predetermined threshold or the rate of change in signal is greater than a predetermined threshold. In this manner, mechanical sensing module 87 may be able to reduce the required bandwidth of processor 80.

Sensor 41 may take the form of any type of sensor that can detect mechanical movement or pressure. In one example, sensor 41 comprises a pressure sensor that measures blood pressure. The pressure sensor may be positioned to detect blood pressures within the right or left ventricle. Alternatively, the pressure sensor may be positioned adjacent to a systemic artery to detect the systemic pressure wave produced by the contracting left ventricle. In another example, sensor 41 comprises an accelerometer that detects movement of a ventricle wall. The accelerometer, or multiple accelerometers, may be directly attached to the interior or exterior wall of a ventricle. Alternatively, the accelerometer may be attached near the distal end of one of leads 18, 20, or 22. As the accelerometer moves on the lead with each movement of the ventricles, the signal generated by the accelerometer may vary.

Although sensor 41 is shown as physically coupled to IMD 16, sensor 41 may comprise a wireless sensor. The wireless sensor may be implanted at a desired location within or on patient 14 and communicate wirelessly with IMD 16. In some examples, IMD 16 communicates with multiple wireless sensors to acquire data related to the occurrence of the ventricular mechanical event.

In some examples, processor 80 determines an A-V interval for timing the delivery of a pre-excitation stimulus to infarct tissue relative to the occurrence of an electrical event, e.g., delivery of pacing or intrinsic depolarization, in the atria. Processor 80 determines the A-V interval for pre-excitation stimulation in subsequent cardiac cycles based on the timing of the sensed mechanical ventricular event in cycles in which pre-excitation stimulus is not delivered to the infarct tissue. In particular, processor 80 determines the A-V interval by subtracting a pre-excitation interval (PEI) from an interval between the atrial event and a subsequent (resulting) mechanical event in the ventricle, e.g., onset of mechanical contraction, which may be referred to as the A-$V_m$ interval, during cardiac cycles in which pre-excitation stimulus is not delivered.

Processor 80 stores the determined A-$V_m$ intervals and A-V intervals in memory 82. Processor 80 also stores a value for the PEI 92 for determining the A-V interval from the determined A-$V_m$ intervals in memory 82. The value of PEI 92 may be predetermined, user programmable via programmer 24 and telemetry module 88, and may be automatically updated by processor 80 as described below.

Generally, PEI 92 is between approximately 0 millisecond and approximately 250 milliseconds. PEI 92 may be between approximately 30 milliseconds and approximately 140 milliseconds. If a current A-V interval determined based on a current PEI 92 is not effective at synchronizing the infarct tissue with the surrounding healthy cardiac tissue, processor 80 may increase the pre-excitation interval by an additional 5 milliseconds, for example. Processor 80 may continue this process until the infarct tissue is effectively treated.

Alternatively, processor 80 may determine PEI 92 as a percentage of the measured A-$V_m$ interval. For example, processor 80 may set PEI 92 as approximately five percent of the A-$V_m$ interval. Processor 80 may then increase PEI 92 as necessary to effectively treat the infarct tissue. Generally, PEI 92 may be between approximately 0 and approximately 80 percent of the A-$V_m$ interval. More specifically, the PEI 92 may be between approximately 3 and approximately 20 percent of the A-$V_m$ interval. A user may be authorized to override any processor 80 determined PEI 92 via programmer 24. Determining PEI 92 as a percentage of the measured A-$V_m$ interval may allow the A-V interval for pre-excitation stimuli to track changes in the measured A-$V_m$ interval due to changes in heart rate, e.g., caused increased patient activity or exertion.

Heart 12 may respond differently depending on whether the atrial depolarization is paced or intrinsic. Accordingly, processor 80 may determine and memory 82 may store separate A-$V_m$ intervals 94A and 94B and A-V intervals 96A and 96B depending on whether the atrial depolarization was paced or intrinsic. A-$V_m$ intervals 94A and 94B used to determine the A-V intervals may be a mean or median of a plurality of measured A-$V_m$ intervals, such as the mean of the most recent N intervals.

In the illustrated example, processor 80 also determines and memory 82 also stores atrial paced A-$V_m$ intervals 98A and atrial intrinsic A-$V_m$ intervals 98B determined during cardiac cycles when pre-excitation stimulus (PES) is delivered, respectively. As discussed in greater detail below, processor 80 or another processor evaluates the efficacy of the current PEI 92 based on a comparison, e.g., difference or ratio, between A-$V_m$ intervals 98 during pre-excitation stimulation and A-$V_m$ intervals 94 without pre-excitation stimulation. For example, atrial paced A-$V_m$ interval 94A may be compared to atrial paced A-$V_m$ interval 98A, and atrial intrinsic A-$V_m$ interval 94B may be compared to atrial intrinsic A-$V_m$ interval 98B. In general, pre-excitation A-$V_m$ intervals 98 should be less than non-pre-excitation A-$V_m$ intervals 94.

Pre-excitation A-$V_m$ intervals 98 may be a mean or median of a plurality of measured A-$V_m$ intervals, such as the mean of the most recent N intervals.

Other information that may indicate the efficacy of the current PEI 92 includes any information indicative of cardiac output or performance, such as one or more pressures or volumes that indicate cardiac output or performance, as is known the art. IMD 16 may include any one or more sensors to enable processor 80 to determine such metrics of cardiac output or performance.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 to telemetry module 88 and receive data from programmer 24 via telemetry module 88.

For example, processor 80 may transmit atrial paced pre-excitation A-$V_m$ intervals 98A and atrial intrinsic pre-excitation A-$V_m$ intervals 98B, or metrics of cardiac output or performance, to programmer 24 via telemetry module 88. In this manner, a clinician may evaluate the efficacy of a current PEI 92. In some examples, telemetry module 88 may transmit an alert to programmer 24 indicating that a user must select a new PEI 92 or confirm the selection of a new interval by processor 80. In some examples, telemetry module 88 may receive a user specified PEI 92 from programmer 24.

Figure 5:
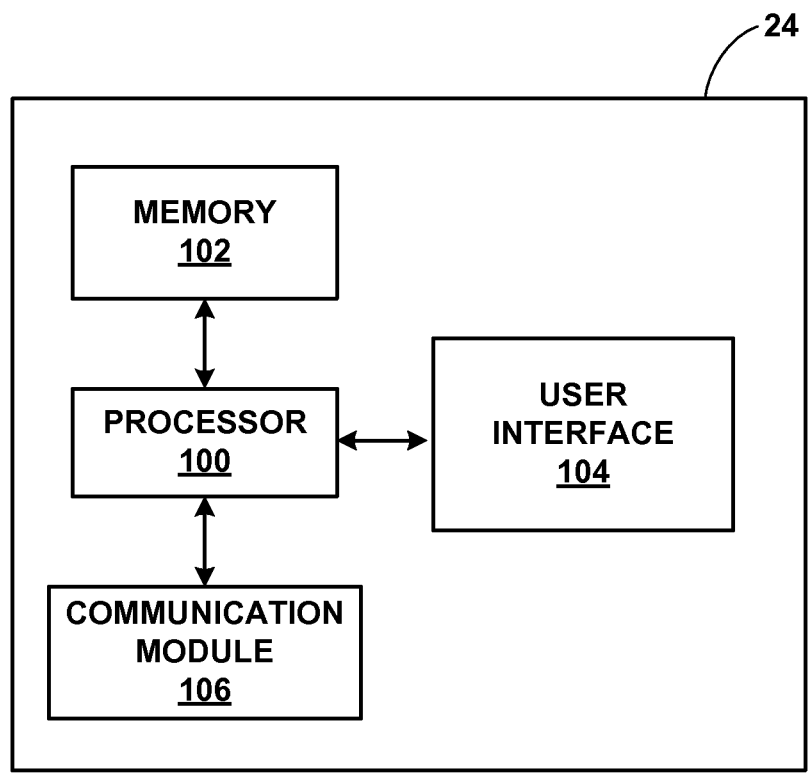
FIG. 5 is a functional block diagram illustrating an example configuration of an external programmer that facilitates user communication with the IMD.

FIG. 5 is a functional block diagram illustrating an example configuration of external programmer 24 that facilitates user communication with IMD 16. As shown in FIG. 5, programmer 24 may include a processor 100, memory 102, user interface 104, and telemetry module 106. Programmer 24 may be a dedicated hardware device with dedicated software for interacting with IMD 16. Alternatively, programmer 24 may be an off-the-shelf computing device running an application that enables programmer 24 to interact with IMD 16.

A clinician may use programmer 24 to review pre-excitation A-$V_m$ intervals 98 and non-pre-excitation A-$V_m$ intervals 94, or metrics of cardiac output or performance, received from IMD 16. In this manner, the clinician may evaluate the efficacy of a current PEI 92. In some examples, processor 100 may provide an alert via user interface 104 indicating that the clinician should select a new pre-excitation interval or confirm an automatically selected PEI 92. In some examples, processor 100 may receive a user-selected PEI 92 via user interface 104, and transmit the PEI to IMD 16 via communication module 106.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 communicates wirelessly with IMD 16, such as using RF communication or proximal inductive interaction. This wireless communication is possible through the use of communication module 106, which may be coupled to an internal antenna or an external antenna. An external antenna that is coupled to programmer 24 may take the form of a programming head that may be placed over heart 12.

Communication module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 100 of programmer 24 and/or one or more processors of one or more networked computers may perform all or a portion of the techniques described herein with respect to processor 80 and IMD 16. For example, processor 100 or another processor may receive, from IMD 16, indications of atrial electrical events and mechanical ventricular events, and determine the intervals 92, 94, 96 and 98 in the manner described with respect to processor 80 and IMD 16.

Figure 6A:
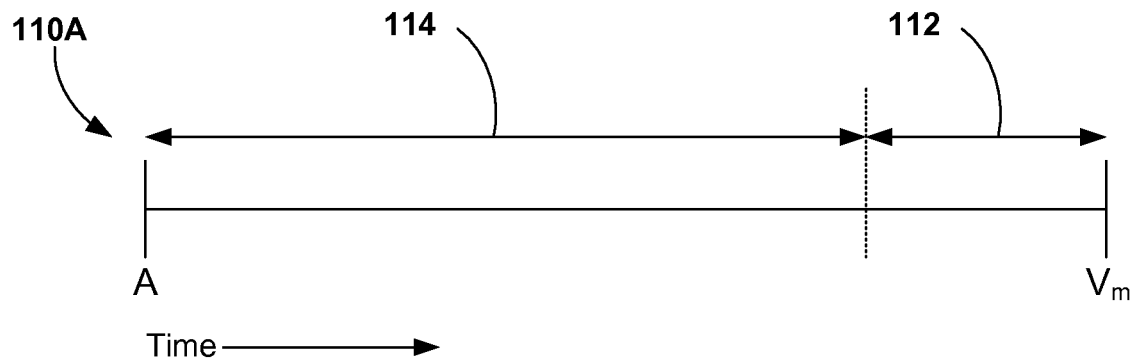
FIGS. 6A and 6B are timing diagrams illustrating an example technique for determining an A-V interval for delivery of a pre-excitation signal to infarct tissue.
Figure 6B:
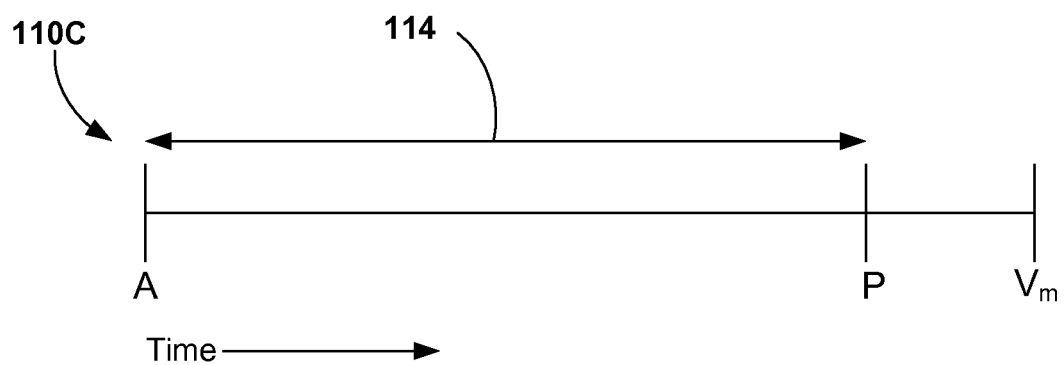

FIGS. 6A and 6B are timing diagrams illustrating an example technique for determining an A-V interval for delivery of a pre-excitation signal to infarct tissue. Diagram 110A in FIG. 6A shows the relationship between the electrical atrial event (A) and the following mechanical event ($V_m$) associated with ventricular contraction for a single cardiac cycle. The mechanical event may be the earliest mechanical activation of the ventricular myocardiam subsequent to the atrial event. The time measured between the atrial event and the mechanical ventricular event is the A-$V_m$. As described herein, the atrial event may be an intrinsic depolarization or an atrial pace delivered by IMD 16. Without a pre-excitation stimulus, any infarct tissue would react to a paced or intrinsic ventricular depolarization after healthy myocardium creates the mechanical event, increasing stress on the infarct tissue and leading to remodeling of heart 12. From the A-$V_m$. interval, IMD 16 has determined an A-V interval 114A by subtracting a PEI 112A.

FIG. 6B illustrates timing diagram 110B of a subsequent cardiac cycle in which a pre-excitation stimulus (P) is delivered to the infarct tissue. IMD 16 delivers the pre-excitation stimulus the A-V interval 114 after detecting the subsequent atrial event in the subsequent cardiac cycle. As illustrated by FIG. 6B, delivery of the pre-excitation stimulus (P) may result in the mechanical ventricular event $V_m$, e.g., onset of ventricular contraction, occurring somewhat earlier relative to the intrinsic $V_m$ of FIG. 6A.

Figure 7:
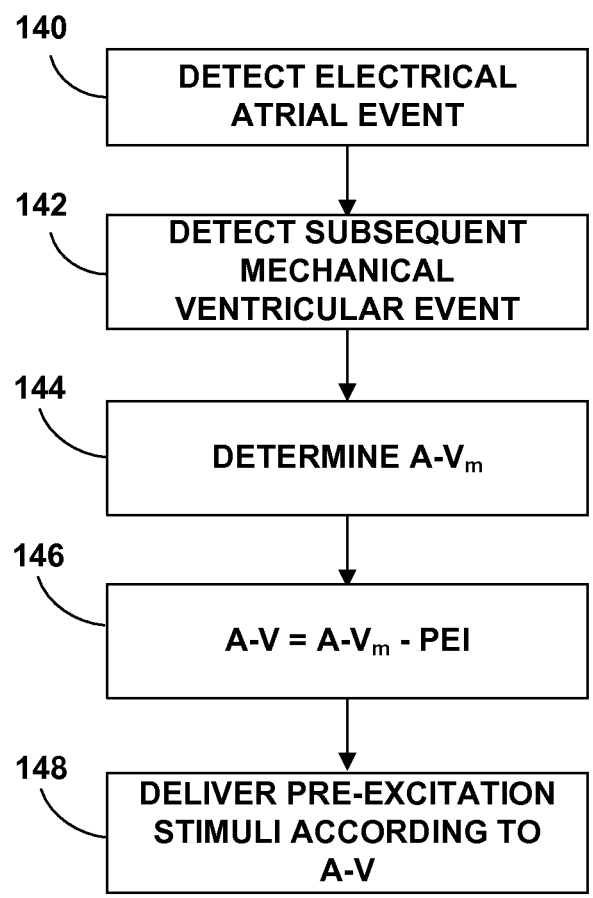
FIG. 7 is a flow diagram illustrating an example method for determining an A-V interval for delivery of a pre-excitation signal to infarct tissue.

FIG. 7 is a flow diagram illustrating an example method for determining an A-V interval for delivery of a pre-excitation signal to infarct tissue. The method of FIG. 7 is described as being performed by IMD 16, e.g., processor 80. However, in other examples, the method is performed, at least in part, by programmer 24 or another computing device.

As illustrated in FIG. 7, processor 80 detects an electrical atrial event (140). The atrial event may be intrinsic depolarization detected by electrical sensing module 86 and indicated to processor 80, or a pacing pulse delivered by signal generator 84 under the control of processor 80. Processor 80 further detects a subsequent mechanical ventricular event, e.g., the onset of ventricular contraction, based on a signal received from sensor 41 (142).

Processor 80 determines the A-V$_m$ 94 as described herein based on the times these events were detected (144). Processor 80 further determines an A-V interval 96 based on the A-V$_m$ 94 and a stored PEI 92 (146). Processor 80 control signal generator 84 to deliver pre-excitation stimuli to infarct tissue during subsequent cardiac cycles according to the A-V interval, e.g., controls the signal generator to deliver pre-excitation stimuli the A-V interval after atrial electrical events in subsequent cardiac cycles (148).

As discussed above, processor 80 may determine separate A-V$_m$ intervals 94A and 94B and A-V intervals 96A and 96B based on whether the detected atrial event is paced or intrinsic. In such examples, processor 80 determines whether the event was paced or intrinsic prior to determining the A-V$_m$ 94A or 94B (144), and also prior to delivering a pre-excitation stimulus during a particular cardiac cycle (148). Processor 80 selects the paced A-V 96A or intrinsic A-V 96B for delivery of a pre-excitation stimulus during a particular cardiac cycle based on whether the atrial event during that cardiac cycle was paced or intrinsic.

Figure 8:
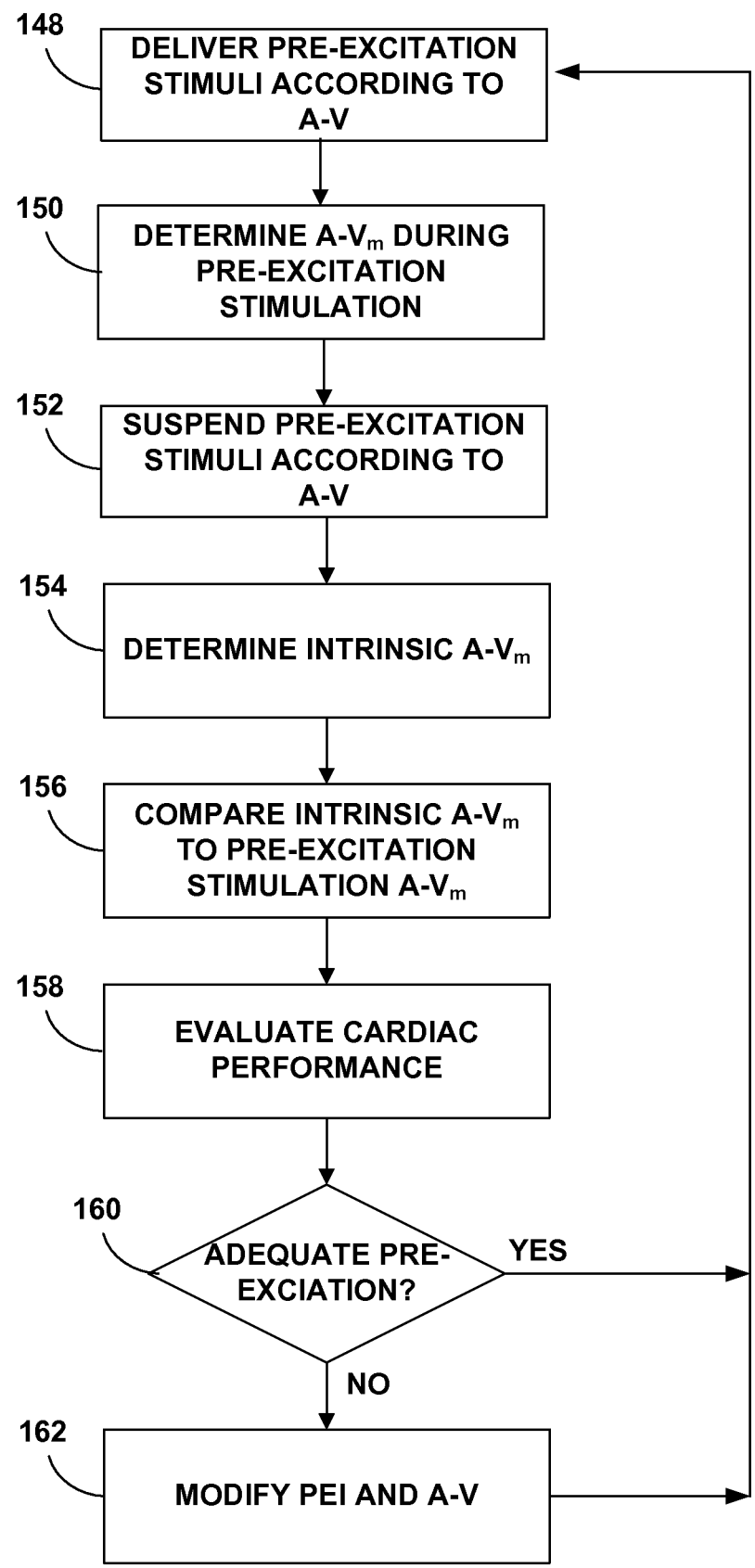
FIG. 8 is a flow diagram illustrating an example method for checking and updating the A-V interval for delivery of a pre-excitation signal to infarct tissue.

FIG. 8 is a flow diagram illustrating an example method for checking and updating the A-V interval for delivery of a pre-excitation signal to infarct tissue. The method of FIG. 8 is described as being performed by IMD 16, e.g., processor 80. However, in other examples, the method is performed, at least in part, by programmer 24 or another computing device.

IMD 16 delivers pre-excitation stimuli according to the A-V interval 96, as described above with respect to FIG. 7 (148). During delivery of pre-excitation stimulation, processor 80 receives indication of electrical atrial events and mechanical ventricular events from sensing module 86 and sensor 41. Processor 80 determines the A-V$_m$ during pre-excitation stimulation based on atrial pacing (98A) or intrinsic atrial activity (98B) and the timing of these events (150).

Processor 80 periodically suspends delivery of pre-excitation stimulation, e.g., controls signal generator 84 to suspend delivery of the pre-excitation stimulation (152). During this time, processor 80 determines the A-V$_m$ without pre-excitation stimulation (94), using the techniques described above with respect to items 140-146 in FIG. 7 (154). Processor 80 compares the stimulated A-V$_m$ 98 with the intrinsic A-V$_m$ 94, e.g., to determine whether the stimulated A-V$_m$ 98 is shorter than the intrinsic A-V$_m$ 94, indicating that the pre-excitation stimuli is delivered prior to onset of intrinsic or paced ventricular contraction (156). Based on signals received from one or more sensors, processor 80 may also evaluate other metrics of cardiac performance during pre-excitation stimulation, such as cardiac output, intracardiac pressures such as left-ventricular end diastolic pressure, or cardiac or cardiovascular flow rates or volumes, which may indicate whether the pre-excitation stimulation is reducing stress at the infarct site and slowing or reversing myocardial remodeling (158).

Based on the comparison and the evaluation (156 and 158), processor 80 determines whether the pre-excitation is adequate (160). If the pre-excitation is adequate, processor 80 controls signal generator 84 to resume delivery of pre-excitation stimuli to the infarct tissue according to the previously determined A-V interval (148). If the pre-excitation is inadequate processor 80 modifies, e.g., increases, the PEI 92, and determines a new A-V interval 96 based on the modified PEI 92 (162). Processor 80 then controls signal generator 84 to resume delivery of pre-excitation stimuli to the infarct tissue according to the modified A-V interval 96 (148).

In some examples, whether or not the PEI 92 is modified, processor 80 updates A-V$_m$ values 94A and 94B based on the intrinsic A-V$_m$ intervals determined during suspension of pre-excitation stimulation. In such examples, processor 80 may calculate new A-V intervals 96A and 96B based on the updated A-V$_m$ intervals and the unmodified PEI. Processor 80 then controls signal generator 84 to resume delivery of pre-excitation stimuli to the infarct tissue according to the modified A-V interval 96 (148).

Determining if the A-V interval needs to be modified according to the above techniques may be done according to a regular schedule, in response to a therapy change, or in response to abnormal cardiac activity. For example, the pre-excitation stimulation may be suspended for such a check on the order of every thirty seconds, every minute, every hour, once a day, or the like.

If PEI 92 of the A-V interval 96 was changed, processor 80 may deliver an alert to programmer 24 or other device to indicate the change. In some examples, a new PEI or A-V interval may not be implemented into therapy until it is confirmed by the user of programmer 24.

Figure 9:
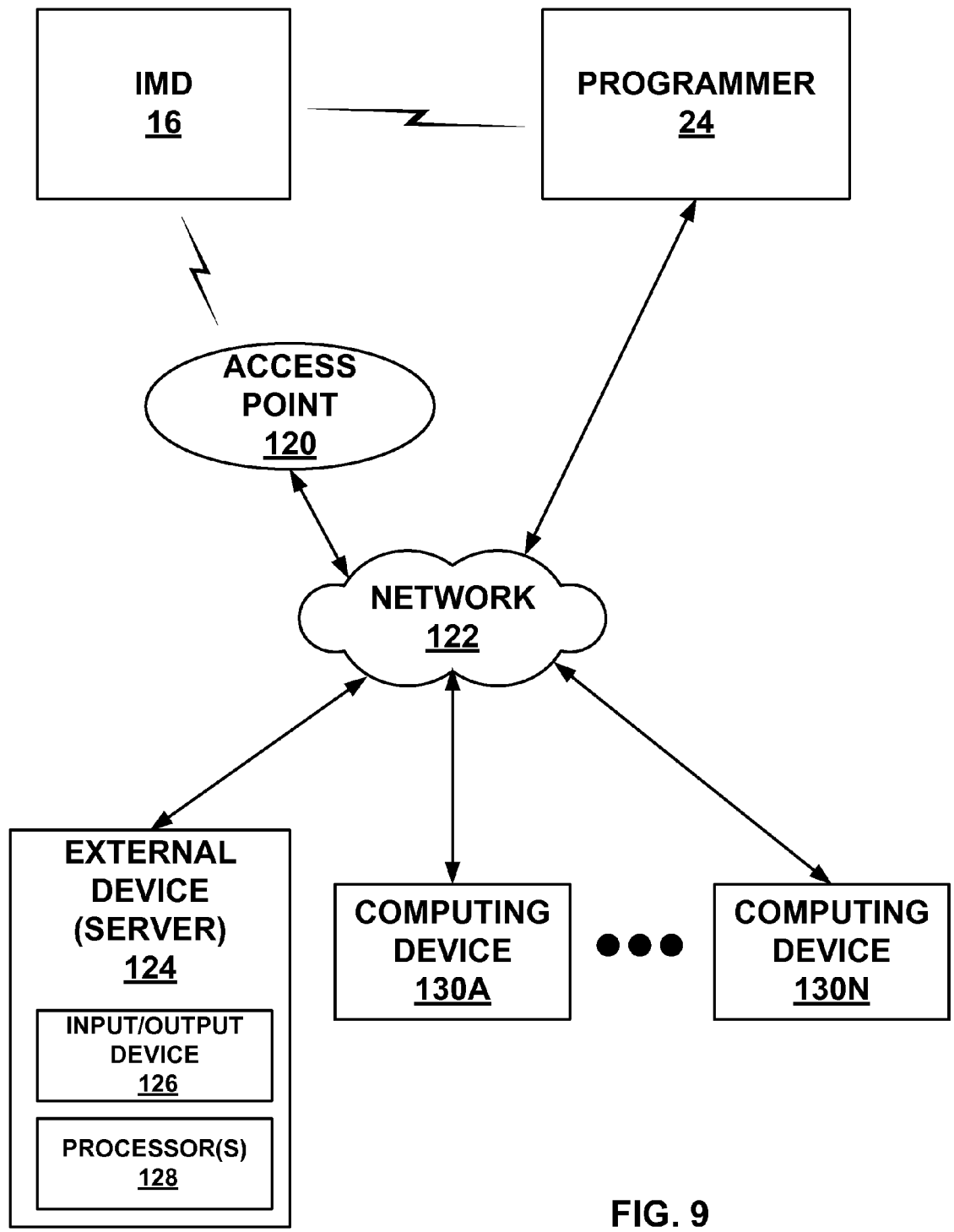
FIG. 9 is a block diagram illustrating an example system that includes an external device, such as a server, and one or more computing devices that are coupled to the IMD and programmer shown in FIG. 1 via a network.

FIG. 9 is a block diagram illustrating an example system that includes an external device, such as a server 124, and one or more computing devices 130A-130N, that are coupled to the IMD 16 and programmer 24 shown in FIG. 1 via a network 122. In this example, IMD 16 may use its telemetry module 88 to communicate with programmer 24 via a first wireless connection, and to communication with an access point 120 via a second wireless connection. IMD 16 and/or programmer 24 may transmit any therapy information associated with patient 14, such as the detected mechanical event, cardiac delay, and pre-excitation interval.

In the example of FIG. 9, access point 120, programmer 24, server 124, and computing devices 130A-130N are interconnected, and able to communicate with each other, through network 122. In some cases, one or more of access point 120, programmer 24, server 124, and computing devices 130A-130N may be coupled to network 122 through one or more wireless connections. IMD 16, programmer 24, server 124, and computing devices 130A-130N may each comprise one or more processors, such as one or more microprocessors, DSPs, ASICs, FPGAs, programmable logic circuitry, or the like, that may perform various functions and operations, such as those described herein.

Access point 120 may comprise a device that connects to network 122 via any of a variety of connections, such as telephone dial-up, digital subscriber line (DSL), or cable modem connections. In other embodiments, access point 120 may be coupled to network 122 through different forms of connections, including wired or wireless connections. In some embodiments, access point 120 may be co-located with patient 14 and may comprise one or more programming units and/or computing devices (e.g., one or more monitoring units) that may perform various functions and operations described herein. For example, access point 120 may include a home-monitoring unit that is co-located with patient 14 and that may monitor the activity of IMD 16.

In some examples, server 124 or computing devices 130 may perform any of the various functions or operations described herein. As shown in FIG. 9, server 124 may include an input/output device 126 and processors 128, similar to programmer 24. A user may interact with server 124 via input/output device 126, similar to programmer 24. In addition, processors 128 may perform any calculations, data processing, communication relay, or any other task required to treat or monitor patient 14.

For example, server 124, computing devices 130, processor 100 or another processor may receive, from IMD 16, indications of the timing of electrical atrial events and mechanical ventricular events, determine the A-V interval for delivery of pre-excitation stimuli based on the indications, and communicate the determined A-V interval to IMD 16 to control the delivery of pre-excitation stimuli. Server 124 may additionally provide the functionality of a user interface with IMD 16, as described with respect to programmer 24.

In some cases, server 124 may be configured to provide a secure storage site for archival of information as related to patient 14 that has been collected from IMD 16 and/or programmer 24. Network 122 may comprise a local area network, wide area network, or global network, such as the Internet. In some cases, programmer 24 or server 124 may assemble information in web pages or other documents for viewing by and trained professionals, such as clinicians, via viewing terminals associated with computing devices 130A-130N. The system of FIG. 9 may be implemented, in some aspects, with general network technology and functionality similar to that provided by the Medtronic CareLink® Network developed by Medtronic, Inc., of Minneapolis, Minn.

Various examples have been described. These and other examples are within the scope of the following claims. For example, although pre-excitation stimuli and pre-excitation intervals are directed herein to cardiac therapy, this disclosure may also be applicable to other therapies in which pre-excitation may be beneficial for damaged tissue. These therapies may include spinal cord stimulation, deep brain stimulation, pelvic floor stimulation, gastric stimulation, occipital stimulation, functional electrical stimulation, and any other stimulation therapy utilizing electrode sensing methods.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
   detecting a mechanical ventricular event during a cardiac cycle of a heart;
   determining a timing of the detected mechanical ventricular event during the cardiac cycle;
   determining a time for delivery of a pre-excitation stimulus to infarct tissue in a ventricle of the heart during a second cardiac cycle based on the timing of the detected mechanical ventricular event; and
   delivering the pre-excitation stimulus to the infarct tissue at the determined time during the subsequent cardiac cycle; and
   wherein determining the time for delivery of the pre-excitation stimulus comprises:
   measuring an $A-V_m$, interval between an atrial event during the cardiac cycle and the mechanical ventricular event during the cardiac cycle; and
   determining an A-V interval based upon the $A-V_m$ interval and
   wherein delivering the pre-excitation stimulus to the infarct tissue at the determined time comprises:
   detecting the atrial event during the subsequent cardiac cycle; and
   delivering the pre-excitation stimulus to the infarct tissue at the A-V interval after the detection;
   wherein determining the A-V interval based upon the $A-V_m$ interval comprises subtracting a re-excitation interval from the $A-V_m$ interval; and
   further comprising:
   evaluating efficacy of the pre-excitation stimulus; and
   modifying the pre-excitation interval based on the evaluation; and
   wherein the measured $A-V_m$ interval comprises a first $A-V_m$ interval measured in the absence of the pre-excitation stimulation, and evaluating the efficacy of the pre-excitation stimulus comprises:
   measuring a second $A-V_m$ interval during pre-excitation stimulation; and
   comparing the first and second intervals, and
   wherein modifying the pre-excitation interval based on the evaluation comprises increasing the pre-excitation interval if the first $A-V_m$ interval is less than or equal to the second $A-V_m$ interval.

2. The method of claim 1, wherein the atrial event comprises one of an intrinsic atrial depolarization or delivery of a pacing pulse to the atria.

3. A method comprising:
   detecting a mechanical ventricular event during a cardiac cycle of a heart;
   determining a timing of the detected mechanical ventricular event during the cardiac cycle;

determining a time for delivery of a pre-excitation stimulus to infarct tissue in a ventricle of the heart during a second cardiac cycle based on the timing of the detected mechanical ventricular event; and delivering the pre-excitation stimulus to the infarct tissue at the determined time during the subsequent cardiac cycle; and wherein determining the time for delivery of the pre-excitation stimulus comprises:

measuring an $A-V_m$, interval between an atrial event during the cardiac cycle and the mechanical ventricular event during the cardiac cycle; and determining an A-V interval based upon the $A-V_m$ interval and wherein delivering the pre-excitation stimulus to the infarct tissue at the determined time comprises:

detecting the atrial event during the subsequent cardiac cycle; and delivering the pre-excitation stimulus to the infarct tissue at the A-V interval after the detection;

wherein the atrial event comprises one of an intrinsic atrial depolarization or delivery of a pacing pulse to the atria; and further comprising detecting a plurality of atrial events during a plurality of cardiac cycles, wherein the atrial events include at least one intrinsic atrial depolarization and at least one pacing pulse, wherein measuring an $A-V_m$ interval comprises:

measuring a first $A-V_m$ interval from the intrinsic atrial depolarization to a first ventricular mechanical event in a first cardiac cycle; and measuring a second $A-V_m$ interval from the pacing pulse to a second ventricular mechanical event in a second cardiac cycle, wherein determining an A-V interval based upon the $A-V_m$ interval comprises determining a first A-V interval based upon the first $A-V_m$ interval and a second A-V interval based upon the second $A-V_m$ interval, wherein detecting the atrial event during the subsequent cardiac cycle comprises determining whether the atrial event comprises an intrinsic atrial depolarization or delivery of a pacing pulse to the atria, and wherein delivering the pre-excitation stimulus to the infarct tissue at the A-V interval after the detection comprises:

selecting the first or second A-V interval based on the determination of whether the atrial event comprises the intrinsic atrial depolarization or delivery of the pacing pulse to the atria; and delivering the pre-excitation stimulus to the infarct tissue at the selected A-V interval after the detection of the atrial event.

4. A method according to claim 1, wherein the mechanical ventricular event comprises onset of ventricular contraction.

5. The method of claim 4, wherein detecting the ventricular mechanical event comprises at least one of sensing motion of a lead attached to the heart, sensing ventricle wall motion, sensing systemic blood pressure, or sensing intra-ventricular pressure.

6. A system comprising:

a medical device configured to deliver a pre-excitation stimulus to infarct tissue in a ventricle of a heart of a patient;

a sensor configured to generate a signal that varies as a function of mechanical ventricular activity; and a processor configured to detect a mechanical ventricular event during a cardiac cycle of the heart based on the sensor signal, determining a timing of the mechanical ventricular event during the cardiac cycle, determine a time for delivery of the pre-excitation stimulus during a subsequent cardiac cycle based on the detected mechanical ventricular event, and control the medical device to deliver the pre-excitation stimulus to the infarct tissue at the determined time during the subsequent cardiac cycle; and wherein the processor measures an $A-V_m$ interval between an atrial event during the cardiac cycle and the mechanical ventricular event during the cardiac cycle determines an A-V interval based upon the measured $A-V_m$ interval detects the atrial event during the subsequent cardiac cycle, and delivers the pre-excitation stimulus to the infarct tissue at the A-V interval after the detection;

wherein the processor subtracts a pre-excitation interval from the $A-V_m$ interval to determine the A-V interval;

wherein the processor evaluates efficacy of the pre-excitation stimulus, and modifies the pre-excitation interval based on the evaluation; and wherein the measured $A-V_m$ interval comprises a first $A-V_m$ interval measured in the absence of the pre-excitation stimulation, and the processor measures a second $A-V_m$ interval during pre-excitation stimulation, compares the first and second intervals, and increases the pre-excitation interval if the first $A-V_m$ interval is less than or equal to the second $A-V_m$ interval.

7. The system of claim 6, wherein the processor calculates the pre-excitation interval as a percentage of the $A-V_m$ interval.

8. A system according to claim 6, wherein the mechanical ventricular event comprises onset of ventricular contraction.

9. The system of claim 6, wherein the sensor comprises at least one of a pressure sensor senses at least one of systemic blood pressure or intra-ventricular blood pressure, an accelerometer attached to a cardiac a lead coupled to the heart, or an accelerometer attached to a ventricular wall of the heart.

10. The system of claim 6, further comprising an intracardiac lead coupled to the medical device, wherein the lead comprises the sensor and at least one electrode, wherein the medical device delivers the pre-excitation stimulus via the electrode.

11. The system of claim 6, wherein the medical device comprises an implantable medical device.

12. The system of claim 11, wherein the implantable medical device comprises at least one of a pacemaker, a cardioverter, or a defibrillator.

13. The system of claim 11, wherein the processor comprises a processor of the medical device.

14. A method comprising:

detecting a mechanical ventricular event during a cardiac cycles of a heart;

measuring a first $A-V_m$ interval in the absence of the pre-excitation stimulation between an atrial event during the cardiac cycle and the mechanical ventricular event during the cardiac cycle and determining an A-V interval based upon the $A-V_m$ interval, wherein determining the A-V interval based upon the $A-V_m$ interval comprises subtracting a pre-excitation interval from the $A-V_m$ interval;

delivering pre-excitation stimulation and measuring a second $A-V_m$ interval during pre-excitation stimulation comparing the first and second $A-V_m$ intervals, and modifying the pre-excitation interval based on the evaluation by increasing the pre-excitation interval if the first A-V$_m$ interval is less than or equal to the second A-V$_m$ interval;

detecting an atrial event during the subsequent cardiac cycle; and delivering the pre-excitation stimulus to infarct tissue at the A-V interval after the detection.

15. A method comprising:

detecting mechanical ventricular events during cardiac cycles of a heart;

detecting a plurality of atrial events during a plurality of cardiac cycles, wherein the atrial events include at least one intrinsic atrial depolarization and at least one pacing pulse;

measuring a first A-V$_m$ interval from the intrinsic atrial depolarization to a first said ventricular mechanical event in a first cardiac cycle; and measuring a second A-V$_m$ interval from the pacing pulse to a second said ventricular mechanical event in a second cardiac cycle, determining a first A-V interval based upon the first A-V$_m$ interval and a second A-V interval based upon the second A-V$_m$ interval, detecting an atrial event during a subsequent cardiac cycle, comprising determining whether the atrial event comprises an intrinsic atrial depolarization or delivery of a pacing pulse to the atria, and delivering the pre-excitation stimulus to the infarct tissue at the A-V interval after the detection, comprising:

selecting the first or second A-V interval based on the determination of whether the atrial event comprises the intrinsic atrial depolarization or delivery of the pacing pulse to the atria; and delivering the pre-excitation stimulus to the infarct tissue at the selected A-V interval after the detection of the atrial event.

16. A system comprising:

a medical device configured to deliver a pre-excitation stimulus to infarct tissue in a ventricle of a heart of a patient;

a sensor configured to generate a signal that varies as a function of mechanical ventricular activity; and a processor configured to:

detect mechanical ventricular events during a plurality of cardiac cycles of the heart based on the sensor signal detect a plurality of atrial events during the plurality of cardiac cycles, wherein the detected atrial events include at least one intrinsic atrial depolarization and at least one pacing pulse;

measure a first A-V$_m$ interval from the intrinsic atrial depolarization to a first said ventricular mechanical event in a first cardiac cycle and determine an A-V interval wherein the processor subtracts a pre-excitation interval from the first A-V$_m$ interval to determine the A-V interval;

measuring a second A-V$_m$ interval from the pacing pulse to a second said ventricular mechanical event in a second cardiac cycle, compare the first and second A-V$_m$ intervals, and increase the pre-excitation interval if the first A-V$_m$ interval is less than or equal to the second A-V$_m$ interval; and deliver the pre-excitation stimulus to the infarct tissue at the A-V interval after the detection of an atrial event is a subsequent cardiac cycle.

* * * * *